(12) United States Patent
Alesi et al.

(10) Patent No.: US 6,582,397 B2
(45) Date of Patent: Jun. 24, 2003

(54) NEEDLE SAFETY DEVICE WITH ANTIREMOVAL PROTECTION

(75) Inventors: Daniel E. Alesi, Keene, NH (US); Roddi J. Simpson, Antrim, NH (US)

(73) Assignee: Portex, Inc., Keene, NH (US)

( * ) Notice: Subject to any disclaimer, the term of this patent is extended or adjusted under 35 U.S.C. 154(b) by 22 days.

(21) Appl. No.: 09/883,360

(22) Filed: Jun. 19, 2001

(65) Prior Publication Data

US 2002/0193744 A1 Dec. 19, 2002

(51) Int. Cl.[7] .............................. A61M 5/00; A61M 5/32
(52) U.S. Cl. ........................................ 604/110; 604/192
(58) Field of Search ........................... 604/110, 164.08, 604/192, 197, 263; 128/919

(56) References Cited

U.S. PATENT DOCUMENTS

| | | | |
|---|---|---|---|
| 5,496,274 A | * 3/1996 | Graves et al. | 604/192 |
| 5,599,318 A | * 2/1997 | Sweeney et al. | 604/263 |
| 5,681,295 A | * 10/1997 | Gyure et al. | 604/192 |
| 5,957,892 A | * 9/1999 | Thorne | 604/162 |

* cited by examiner

Primary Examiner—Brian L. Casler
Assistant Examiner—Catherine Serke
(74) Attorney, Agent, or Firm—Louis Woo

(57) ABSTRACT

A needle safety device has a collar and a housing pivotally connected thereto. Cooperating locking members are provided at the collar and the respective lower sections of the housing so that, once the housing is pivoted to be in alignment with the collar, the locking members would coactingly mate with each other to thereby retain the housing to the collar. To ensure that the coacting locking members could not be sabotaged by the sidewalls of the housing being deliberately forced away from the collar, barriers in the form of guard flaps or arms are provided at the collar so as to prevent those sections of the sidewall that are susceptible to being forced away from the collar from being exposed. As an added benefit, the guard flaps could be used as an anchor to provide stabilization for the use of a hypodermic needle fitted with the safety needle device of the instant invention during a subcutaneous procedure to a patient.

31 Claims, 5 Drawing Sheets

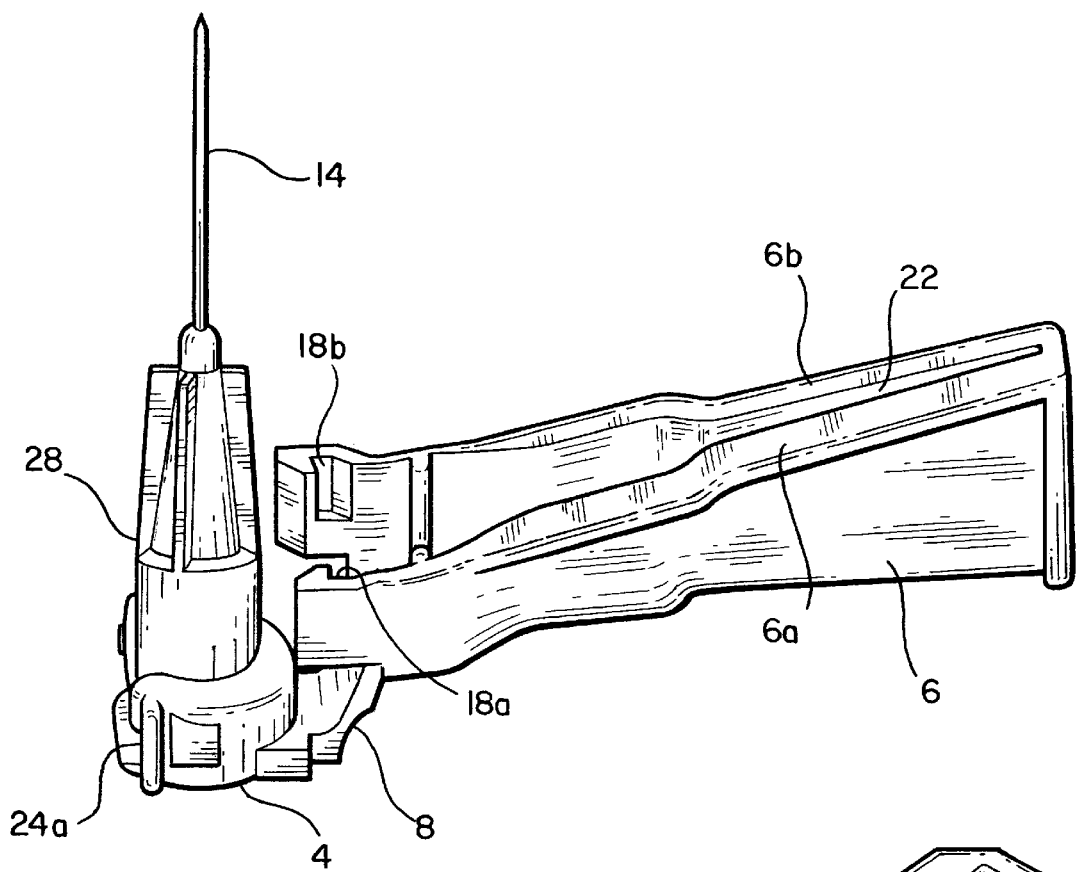
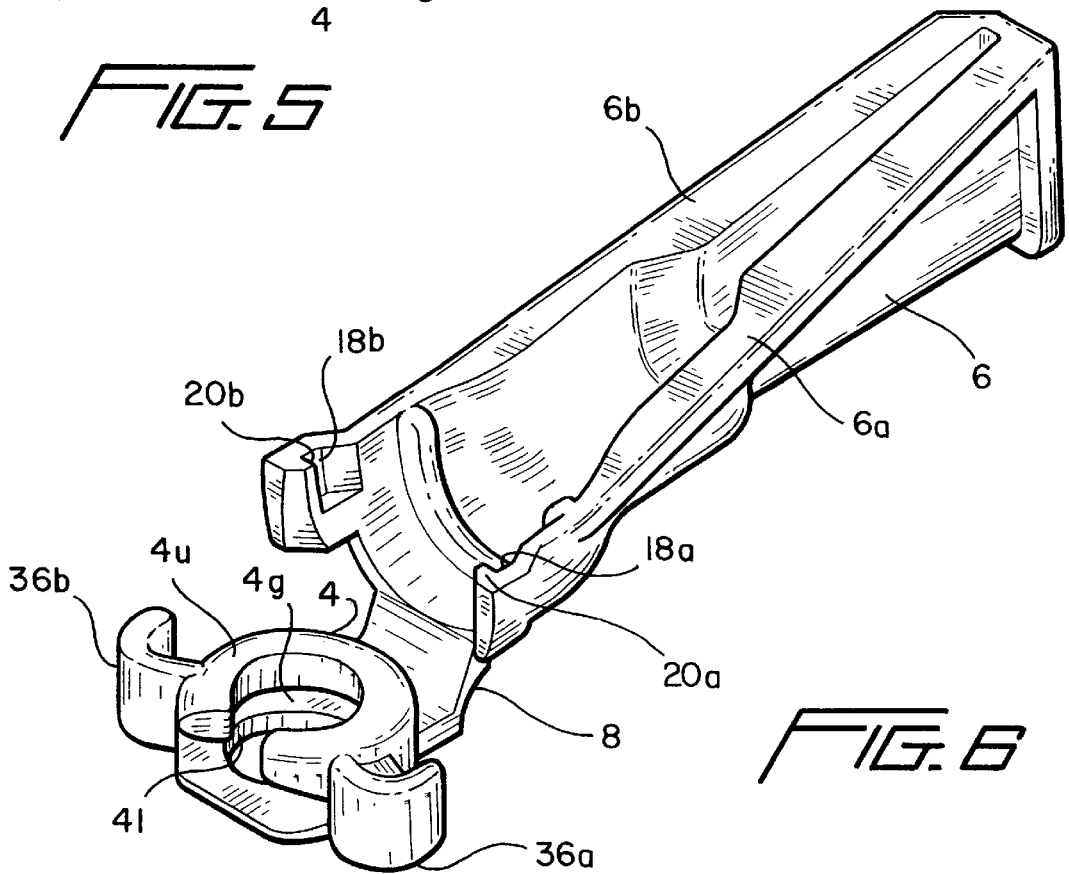

NEEDLE SAFETY DEVICE WITH ANTIREMOVAL PROTECTION

FIELD OF THE INVENTION

This invention relates to a safety device for hypodermic needles and particularly a safety device that has increased protection measures to ensure that a contaminated hypodermic needle is securely enclosed by a needle sheath.

BACKGROUND OF THE INVENTION

The prior art discloses a number of ways in which a hypodermic needle may be prevented from being exposed to the environment. One of these ways is to have a housing that may be pivoted from an open position whereby the needle is exposed to a closed position for enclosing the needle. References that disclose such pivotable housing include the following Hollister U.S. Pat. Nos. 4,982,842; 5,139,489; 5,154,285; 5,232,454; 5,232,455; 5,277,311; 5,423,765; 5,615,771; 5,649,622; 5,993,426 and Re37,110. All of the above noted Hollister U.S. patents are assigned to the same assignee as the instant invention and the respective disclosures of those patents are incorporated by reference herein.

For the prior art needle protection housings, particularly those with the Side Snap feature wherein coacting mechanisms at the base and the housing of the device coact to fixedly retain the housing to the base once the housing is pivoted to a position in alignment with the base, there is always the possibility that some person will deliberately remove the needle protection housing by prying the sidewalls of the housing so that the coacting mechanisms could no longer coact. This is possible due to the fact that the prior art devices are most likely made of plastic and therefore the needle sheath housing would have a built-in elasticity that allows a certain flexing of the sidewalls of the housing. This flexibility is required, on the one hand, to allow the coacting mechanism at the housing to snap over the corresponding coacting mechanism at the base for fixedly retaining the housing to the base. On the other hand, the same flexibility allows a person, if he is intent on sabotaging the integrity of the needle protection device, to pry the housing from the base by applying an extra amount of force, An illustration of the Side Snap feature is best shown in the aforenoted U.S. Pat. Nos. 5,615,771 and 5,649,622.

There is another shortcoming in the prior art needle protection devices. Such shortcoming results from the base, or the collar, of the device being snapped onto the hub or neck of the medical device. Such snap-on feature enables the safety device to rotate about the needle so as to enable the bevel of the needle to be oriented at a best position for use, relative to the needle housing. A device with such snap-on base or collar is best illustrated in the aforenoted U.S. Pat. Nos. 5,142,285 and 5,277,311. The disadvantage of such snap-on collar is the possibility, although unlikely, that a large enough force may be applied, accidentally or otherwise, to the collar of the device so that the device may be dislodged from the hypodermic needle during use.

Yet a further disadvantage of the prior art needle protection devices is that there is a lack of support for use when a patient is being pricked with a needle equipped with the safety device. Oftentimes, during the procedure of either injecting a patient or withdrawing fluid from the patient, particularly when the needle is to be intradermally inserted to the patient, there is a need to provide a support or anchor to stablilize the device as the needle is inserted to the patient. Currently, clinicians have to gauge by experience and instinct how best to stabilize a needle when performing an intradermal procedure on a patient.

SUMMARY OF THE INVENTION

To ensure that a needle protection device with a pivotable housing could not be sabotaged, two guard flaps, or arms are provided to the base of the device to act as barriers to prevent sections of the respective edges of the sidewalls of the housing from being exposed once the housing has been pivoted to be in alignment with the base of the device. In particular, the section of each sidewall of the housing coincides with the area of the housing whereat the locking mechanism for the housing is, and also the location of the coacting locking mechanism at the base, so that once the housing is pivoted to its alignment position and the respective locking mechanisms at the housing and the base coact to retain the housing to the base, it would be difficult for someone to deliberately remove the housing from the base by prying the sidewalls of the housing away from the base.

In a first embodiment, the guard flaps or arms are integrated to the base or collar of the device, and extend from the collar as flat pieces on opposite sides of the collar. The configuration of the guard flaps are such that it would enable a user to use those flaps as anchors or supports for stabilizing the medical device, and more particularly the needle, during a subcutaneous procedure by the user. After the procedure, the guard flaps act as partitions to close off the respective sections of the two sidewalls of the housing, once the housing is pivoted to the alignment position and the corresponding locking members or portions at the housing and collar matingly coact to retain the housing fixedly to the collar.

In a second embodiment, the guard flaps are configured to be curved arms that wrap around at least those sections of the sidewalls of the housing having the locking mechanisms once the housing is pivoted to its alignment position with the collar, to thereby provide even further enclosure for the appropriate sections of the sidewalls of the housing.

A variant of the instant invention safety needle device includes the integration to the housing a latching mechanism such as for example a hook that grasps the needle once the housing is pivoted to the position in alignment with the collar. The hook integral of the housing acts as a redundant safety feature to the Side Snap locking mechanism.

Another feature of the needle safety device of the present invention is the configuration of the base, or collar of the device. Specifically, the collar has an upper portion and a lower portion separated by an internal circumferential groove. The upper portion is an open-ended collar or ring whereas the lower portion is a closed ring. The internal circumferential groove that separates the two portions enables the collar to be fitted to the flange that extends from the base of the needle hub of a conventional hypodermic needle. The internal circumferential groove may be designed with respective tolerances to enable the collar, once fitted to the needle hub of the hypodermic needle, to either rotate about the needle, or stay fixed at a given orientation. If the collar were to stay fixed to the needle hub, it will stay fixed at a given angular orientation relative to the needle hub to position the bevel of the needle to a particular orientation relative to the housing, so as to provide the user with a clear view of the tip of the needle when inserting the needle to the patient. Once the collar is fitted to the needle hub of the hypodermic needle and the luer end of the medical device, be it a syringe or otherwise, the needle safety device is guaranteed to remain coupled to the needle hub insofar as the lower portion of the collar, which is closed, prevents the collar from being removed.

It is therefore an objective of the present invention to provide a needle safety device that has an anti-removal feature which prevents the deliberate removal of a needle protective housing to expose a contaminated needle.

It is yet another objective of the present invention to enable the needle safety device to be used as an anchor in a subcutaneous procedure with a patient.

It is yet another objective of the present invention to provide a needle safety device that, once fitted to the needle hub of a hypodermic needle, would remain fixedly coupled thereto once the luer end of a medical device is fitted to the needle hub of the hypodermic needle.

BRIEF DESCRIPTION OF THE FIGURES

The above mentioned objectives and advantages of the present invention will become apparent and the invention itself will best be understood by reference to the following description of the present invention taken in conjunction with the accompanying drawings, wherein:

FIG. 5 is a side view of a the needle safety device fitted to a hypodermic needle;

FIG. 6 is a second embodiment of the needle safety device of the instant invention;

FIG. 7 is a plan view of the second embodiment of the safety needle device of the instant invention.

DETAILED DESCRIPTION OF THE PRESENT INVENTION

Figure 1:
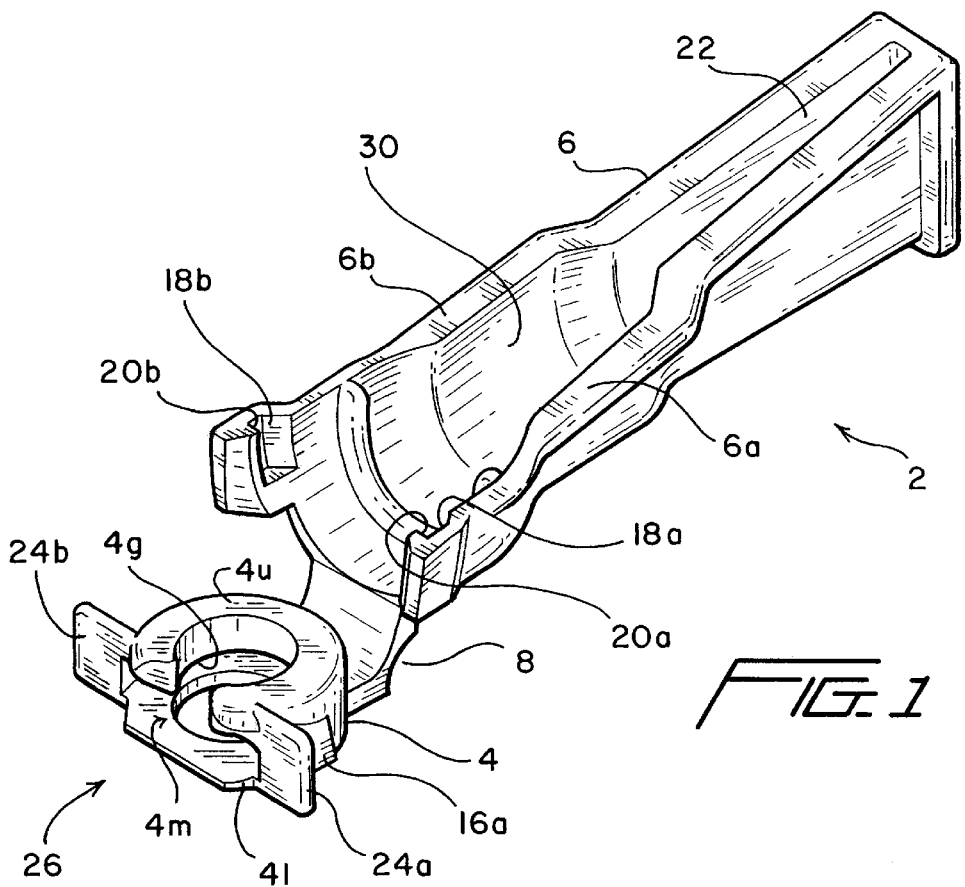
FIG. 1 is a perspective view of a first embodiment of the needle safety device of the instant invention.
Figure 2:
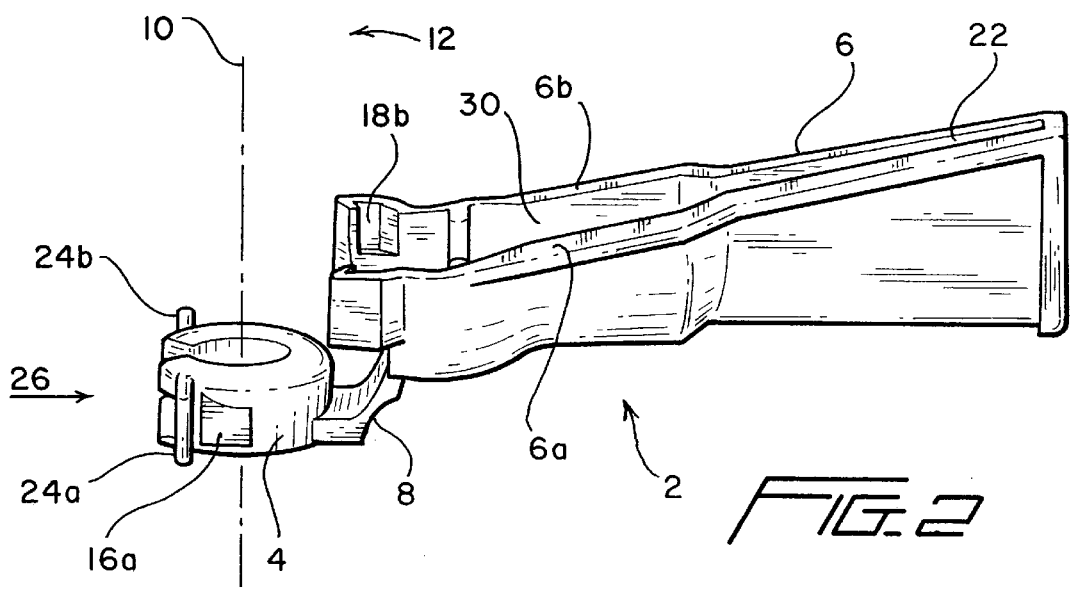
FIG. 2 is a side view of the first embodiment of the present inventive needle protection safety device.
Figure 3:
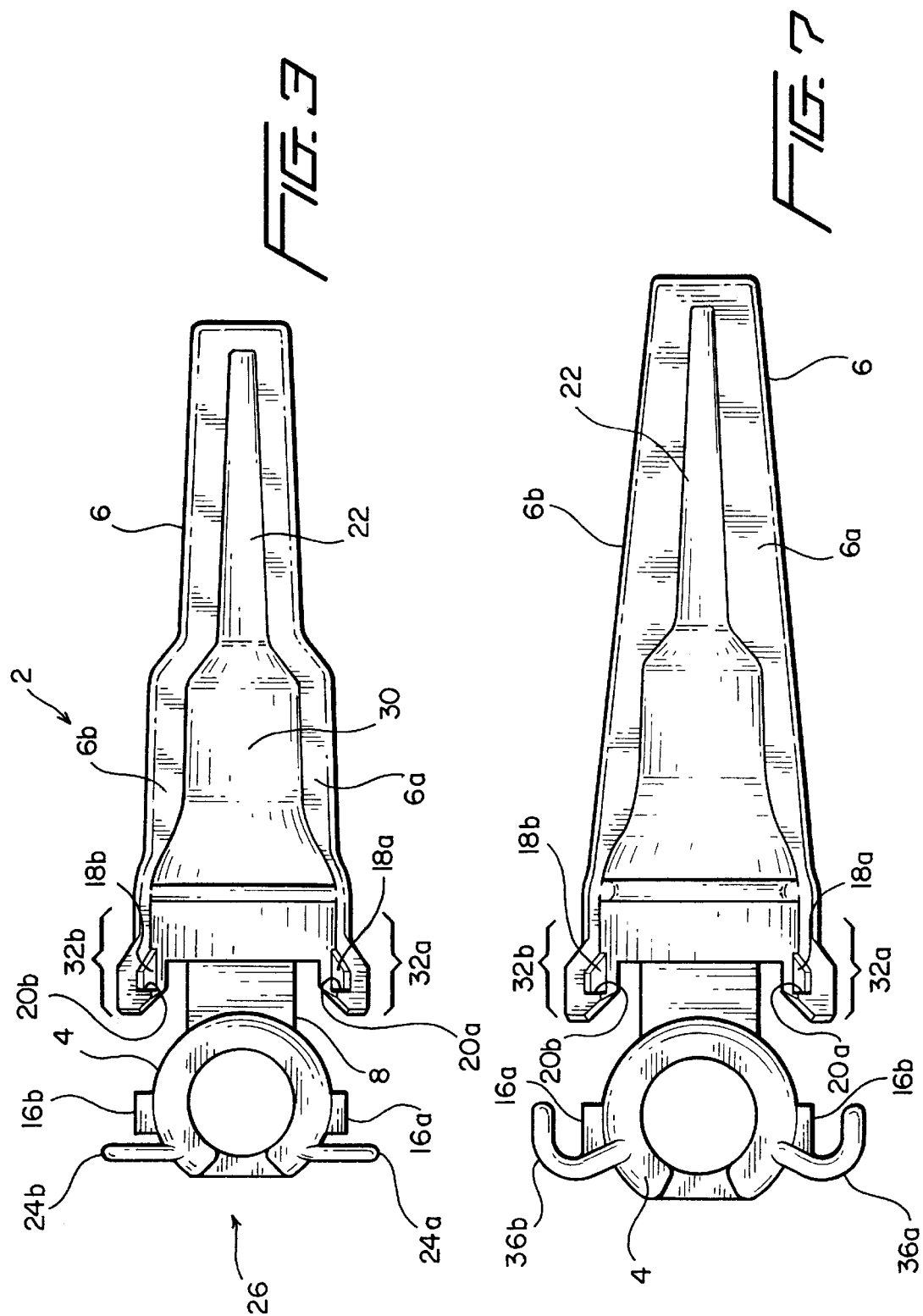
FIG. 3 is a plan view of the first embodiment of the needle safety device of the instant invention.

With reference to FIGS. 1–3, a first embodiment of the needle safety device of the present invention is shown, As illustrated, needle safety device 2 has a base or collar 4 to which is attached a needle sheath or housing 6 by means of a pivotable hinge 8. Base 4 has a longitudinal axis 10 toward which housing 6 is pivotable per shown by directional arrow 12.

Sidewalls 6a and 6b of housing 6 define therebetween a slot 22 wherethrough a needle, such as 14, passes when housing 6 is pivoted to be in an alignment position with base 4. As is disclosed in the aforenoted incorporated by reference patents, housing 6 is pivoted to a position along longitudinal axis 10 so as to be in alignment with base 4, for enclosing a needle such as for example cannula 14, which is a part of a hypodermic needle.

Base 4 has extending at opposite sides thereof two locking portions 16a and 16b. These portions may be in the form of downward sloping members or ears that slant downwards to form a larger base or grasping portion, Each of the ears 16a and 16b coacts with a corresponding locking member formed at the lower portion of housing 6. These locking members are referenced as 18a and 18b, and may be in the form of retaining grooves formed with grasping fingers 20a and 20b, respectively. Thus, when housing 6 is pivoted to the position along longitudinal axis 10 so as to be in alignment with base 4, due to the elasticity of the plastic material from which the needle safety device is manufactured, the respective sidewalls 6a and 6b of housing 6 would flex when it makes contact with the top portion of ears 16a and 16b until fingers 20a and 20b become engaged to the base of ears 16a and 16b, respectively, so that ears 16a and 16b are retained in retaining grooves 18a and 18b, respectively. Once ears 16a and 16b are retained in grooves 18a and 18b, respectively, housing 6 is fixedly retained to base 4.

As best shown in FIGS. 1–3, retaining grooves 18a and 18b, as well as grasping fingers 20a and 20b, are integrally formed in the internal surface of sidewalls 6a and 6b, respectively. Due to the elasticity of the plastic material, prior to the instant invention, if a person were intent to remove housing 6 from base 4, she could do so by applying a great force to the edges of sidewalls 6a and 6b so as to pry the lower portion of housing 6, and therefore coacting locking mechanisms such as 18a, 16a and 18b, 16b from each other. In other words, a person can deliberately sabotage the integrity of the locking mechanism of a prior art needle safety device, if such device is provided with locking mechanisms similar to the Side Snap mechanism illustrated in FIGS. 1–3.

Figure 4:
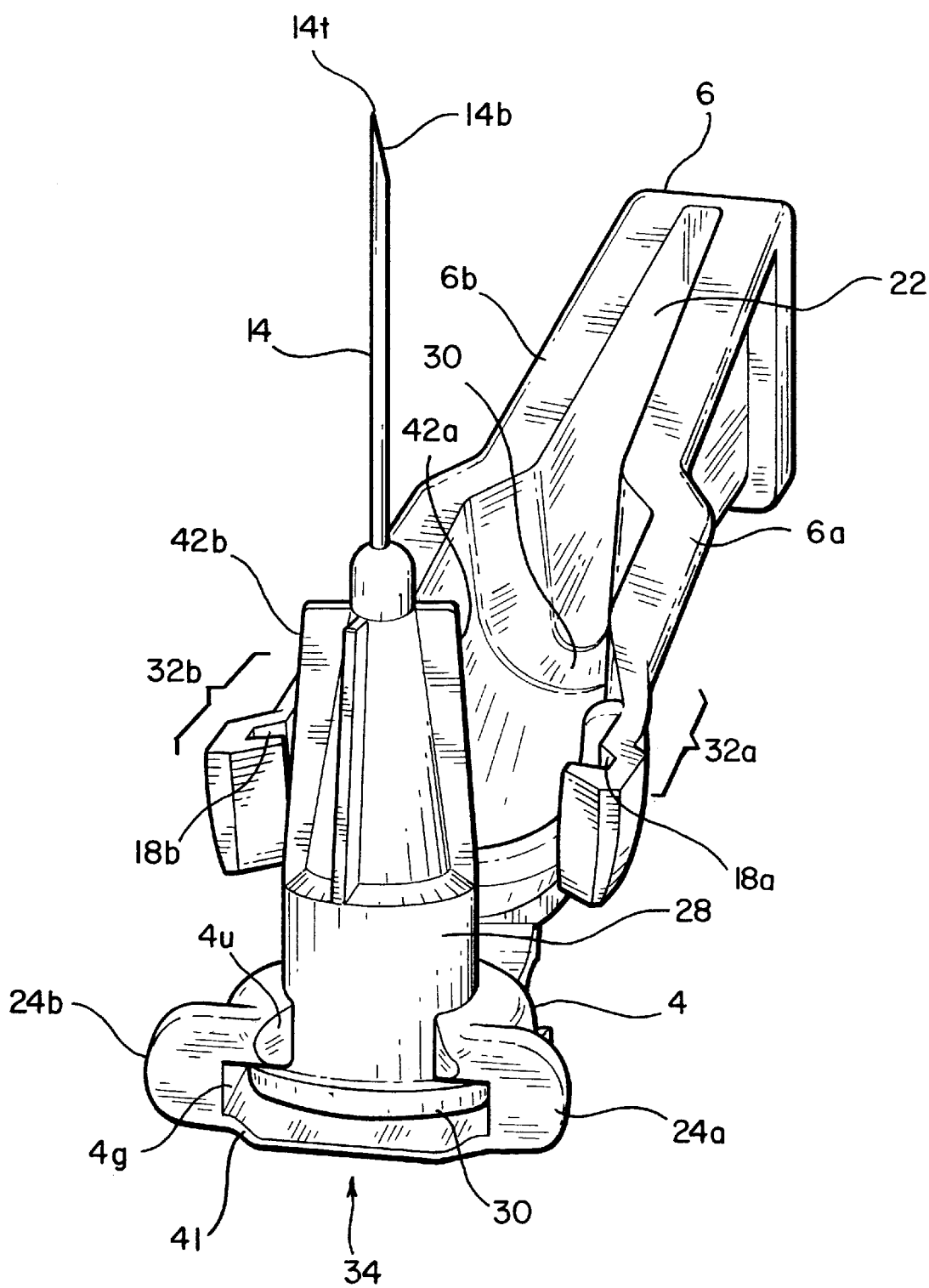
FIG. 4 is a perspective view of the needle safety device fitted to the needle hub of a hypodermic needle.

The present invention substantially eliminates such possibility by providing barrier means in the form of two guarding flaps, or arms, 24a and 24b at the front portion of base 4 opposite to hinge 8, and therefore housing 6. Arms 24a and 24b each extend from base 4 at a location proximate to ears 16a and 16b, respectively, so as to hide or guard those locking members, when viewed in the direction designated by directional arrow 26. Thus, when housing 6 is pivoted to be in alignment with longitudinal axis 10 so that retaining grooves 18a and 18b coact with ears 16a and 16b, respectively, to lock housing 6 to base 4, the edges of the respective sections of sidewall 6a and 6b, which coincide at least with the sections of the sidewalls that have the integral retaining grooves 18a, 18b and gasping fingers 28a and 28b, are hidden when viewed from direction 26. And with a hypodermic needle fitted to needle safety device 2 as shown in FIG. 4 so that the needle hub 28 of the hypodermic needle substantially fills the space 30 of housing 6, it would make it extremely difficult for a person to grasp the lower portions of the edges of sidewall 6a and 6b and deliberately force those sidewalls away from base 4. As best shown in FIG. 4, the sections of sidewalls 6a and 6b that are guarded by arms 24a and 24b are sections 32a and 32b, respectively.

For the embodiment shown in FIGS. 1–3, the fact that guard arms 24a and 24b are flat enables a user to place needle safety device 2 in such a position that arms 24a and 24b are flatly placed against the skin of a patient, during a procedure whereby a user inserts needle 14 intradermal to a patient. Thus, arms 24a and 24b act as anchor means to provide the stabilizing that is desired to prick a patient with a hypodermic needle fitted with the safety needle device of the present invention.

As best shown in FIGS. 1 and 4, base 4 has an internal circumferential groove 4g that separates an upper portion 4u and a lower portion 4l. Both upper portion 4u and lower portion 4l, as is collar 4 itself, are ring shaped. However, upper portion 4u is in the shape of an open collar or ring, while lower portion 4l is a closed ring or collar. Thus, collar 4 has a mouth or opening 4m that is formed by upper portion 4u that leads to internal circumferential groove 4g, which in turn is sandwiched by upper portion 4u and lower portion 4l.

As best shown in FIG. 4, a hypodermic needle, and specifically its needle hub 28, which has a flange 30 extending at its base, is fitted to base 4 by means of mouth 4m from the direction of 26. Internal circumferential groove 4g is configured such that it has a dimension that substantially matches the dimension of flange 30. By design, the dimension of internal circumferential groove 4u could be made wider than flange 30 so that base 4, and therefore housing 6, could be rotated about cannula 14. Alternatively, the dimension of internal circumferential groove 4u could be configured so that, once fitted to base 4, needle hub 28 is frictionally fixed thereto. In the instance where needle hub 28 is fixed, the orientation of needle hub 28 could be calculated so as to ensure that the bevel 14b of cannula 14 has a given orientation, with respect to housing 6, when housing 6 is pivoted away from cannula 14 so that a user can readily see tip 14t of cannula 14 for insertion to the patient. If the dimension of internal circumferential groove 4g is made such that base 4 is rotatable about cannula 4, but with sufficient friction to prevent free rotation, then there is no need to provide any predetermined orientation of bevel 14b, with respect to housing 6.

Given that lower portion 4l of base 4 is a closed ring, when a luer end of a medical device (not shown) is mated to needle hub 28 per directional arrow 34, the hypodermic needle is non-removably mated to collar 4. This prevents needle safety device 2 from being removed, accidentally or otherwise, from the hypodermic needle during use.

FIGS. 6 and 7 illustrate another embodiment of the needle safety device of the instant invention. Components that are the same as in the first embodiment are labeled the same. But for the guard flaps or arms, the embodiment shown in FIGS. 6 and 7 is the same as that shown in the earlier figures. In particular, instead of using flat arms for guarding the coacting locking portions of housing 6 and base 4, the arms for doing so in the embodiment of FIGS. 6 and 7 are curved so that each arm wraps around its corresponding locking portion 16 of base 4. Consequently, when housing 6 is pivoted to be in alignment with base 4 so that locking members 16 and 18 coact to retain housing 6 to base 4, curved arms 36a and 36b prevent to a greater degree the exposure of sections 32a, 32b of respective sidewall 6a, 6b of housing 6. Thus, it makes it even more difficult for a person to deliberately sabotage the integrity of the coacting locking members of housing 6 and base 4.

Figure 8A:
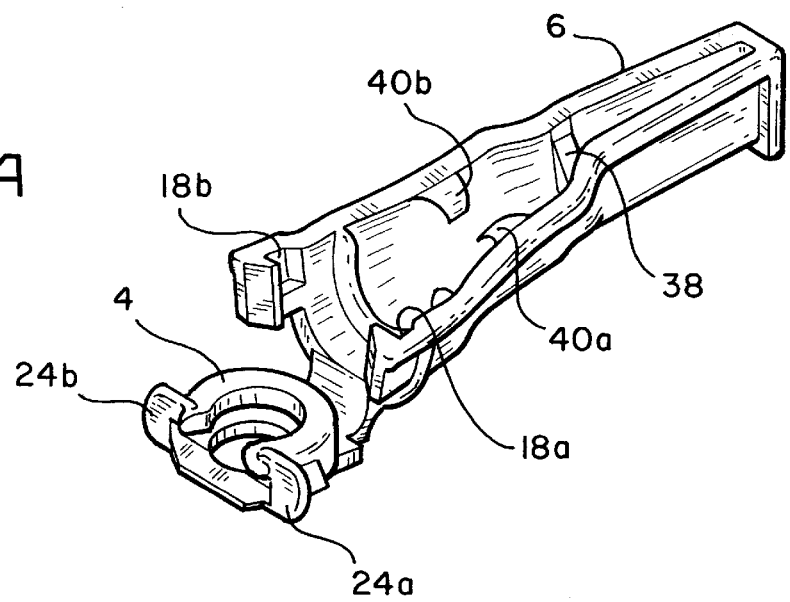
FIG. 8a to FIG. 8c illustrate a different variant of the instant invention in which locking flaps, in addition to both a Side Snap locking mechanism and an internal hook, are provided.
Figure 8B:
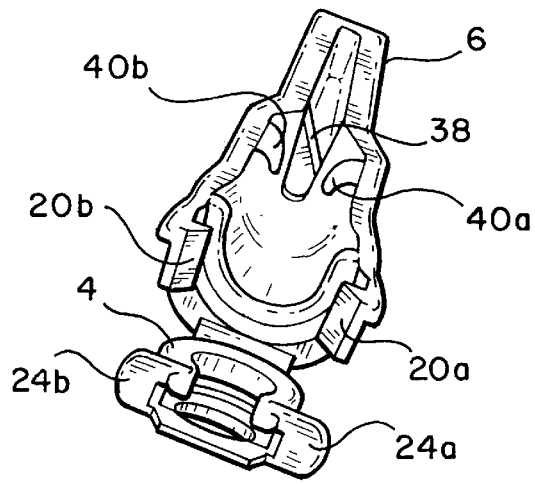
Figure 8C:
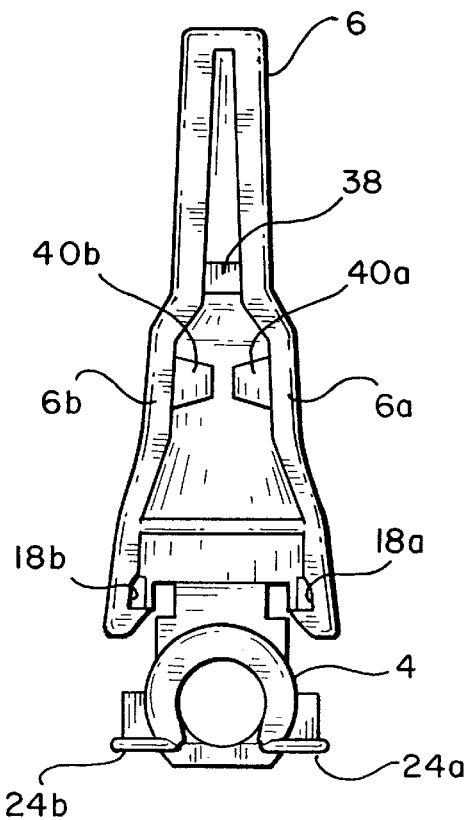

A variant of the needle safety device of the instant invention is shown FIGS. 8a–8c. In this embodiment, in addition to the coacting locking members at housing 6 and base 4, there is also provided a latch mechanism 38, in the form of a hook, integrated to the inside of housing 6. Hook 38 grasps onto the shaft of cannula 14 when housing 6 is pivoted to the alignment position along longitudinal axis 10, and therefore provides a redundant safety locking mechanism for the needle safety device of the instant invention.

In place of, or in conjunction with, hook 38 and the Side Snap locking members, housing 6 may also be provided with flaps 40a and 40b, shown in FIG. 8c, extending internally from sidewalls 6a and 6b, respectively. Flaps 40a and 40b coact with the fins of needle hub 28, such as for example fins 42a and 42b shown in FIG. 4, when housing 6 is pivoted to its alignment position. Flaps 40a and 40b are constructed such that the tips of those flaps are pointed inward toward the back of housing 6 so that the flaps would be biased and pushed down when contacted by fins 42a and 42b as housing 6 is pivoted towards longitudinal axis 10. But once housing 6 is in alignment with longitudinal axis 10 and the respective tips of flaps 40a and 40b clear fins 42a and 42b then flaps 40a and 40b would return to their respective original positions so that each of these flaps would act as an impediment to any reverse pivoting movement of housing 6 from longitudinal axis 10, as flaps 40a and 40b are biased against fins 42a and 42b, respectively.

It should be appreciated that the present invention is subject to many variations, modifications and changes in detail. For example, the barrier guard flaps may be provided to safety devices such as those disclosed in the aforementioned '771 and '622 patents even though the base of the devices disclosed in those patents do not have internal circumferential grooves. Accordingly, it is the intention of the inventors that all matter described throughout this specification and shown in the accompanying drawings be interpreted as illustrative only and not in a limiting sense, Accordingly, it is intended that the invention be limited only by the spirit and scope of the hereto appended claims.

What is claimed is:

1. Apparatus comprising:
    a base having a longitudinal axis;
    a unitary housing pivotable relative to said base having two side walls each having an edge for defining a longitudinal slot therebetween wherethrough a needle passes; and
    a barrier extending from said base to prevent at least one section of the edge of each of said side walls from being exposed once said housing is pivoted relative to said base to be at a position in alignment with said longitudinal axis.

2. Apparatus of claim 1, wherein said base comprises a collar having an internal circumferential groove for mating with a flange extending from a needle hub.

3. Apparatus of claim 1, wherein said barrier comprises two arms each extending from said base orthogonal to the edge of a corresponding one of said side walls once said housing is pivoted to said alignment position.

4. Apparatus of claim 1, wherein said barrier comprises a pair of arms each extending curvedly from said base relative to the edge of a corresponding one of said side walls so as to wrap around a section of the edge of said one side wall once said housing is pivoted to said alignment position.

5. Apparatus of claim 1, further comprising:
    at least one locking member at said base;
    at least an other locking member at said housing;
    wherein said one and other members coactingly mate with each other when said housing is pivoted to said alignment position to prevent said housing from being removed from said base.

6. Apparatus of claim 1, wherein said base is matingly fitted to a hub having a needle extending therefrom, said apparatus further comprising:
    a latch at said housing for fixedly retaining said needle when said housing is pivoted to said alignment position.

7. Apparatus of claim 1, wherein said base comprises a collar that fits about a flange extending from a needle hub, said collar having an internal circumferential groove sandwiched by an upper portion and a lower portion, said upper portion being an open ring and said lower portion being a close ring;
    wherein after said collar is fitted to said needle hub via its internal circumferential groove fitting about said flange and a luer end of a medical device mated to said needle hub, said collar is non-removably mated to said needle hub.

8. Apparatus of claim 1, wherein said barrier comprises two arms at opposite sides of said base each preventing a corresponding sidewall of said housing from being manipulated so that said housing is prevented from being pivoted away from said base once said housing has been pivoted to said alignment position.

9. Apparatus of claim 1, wherein said barrier comprise arms extending from opposite sides of said base, said arms providing support to stabilize a needle extending from a needle hub fitted to said base when said needle is used subcutaneously on a patient.

10. Apparatus of claim 5, wherein said one locking member comprises an ear extending from said base, said apparatus further comprising two ears extending from opposite sides of said base.

11. Apparatus of claim 5, wherein said other locking member comprises a groove, said apparatus further comprising two grooves each integral to one of the two side walls of said housing.

12. Apparatus of claim 5, wherein said other locking member comprises a finger, said apparatus further comprising two fingers each integral to one of the two side walls of said housing.

13. A needle protection apparatus, comprising:
 a collar having first locking portions;
 a housing pivotable relative to said collar, said housing having two side walls each having a second locking portion that coactingly mates with a corresponding one of said first locking portions when said housing is pivoted to a position along a longitudinal axis of said collar;
 a barrier extending from said collar to prevent the respective edges of said side walls of said housing where said second locking portions are located from being exposed once said housing is pivoted to said position along said longitudinal axis.

14. Apparatus of claim 13, wherein said first locking portions comprise respective ears extending from said collar.

15. Apparatus of claim 13, wherein said second locking portions comprise respective grooves or fingers internal of said housing.

16. Apparatus of claim 13, wherein said barrier comprises two arms each extending from said collar in perpendicular relationship to an edge of a corresponding one of said side walls once said housing is pivoted to said position.

17. Apparatus of claim 13, wherein said barrier comprises a pair of arms each extending curvedly from said collar relative to an edge of a corresponding one of said side walls so as to wrap around a section of the edge of said one side wall once said housing is pivoted to said position.

18. Apparatus of claim 13, wherein said collar is matingly fitted to a hub having a needle extending therefrom, said apparatus further comprising:
 a latch at said housing for fixedly retaining said needle when said housing is pivoted to said alignment position.

19. Apparatus of claim 13, wherein said collar fits about a flange extending from a needle hub, said collar having an internal circumferential groove sandwiched by an upper portion and a lower portion, said upper portion being an open ring and said lower portion being a close ring;
 wherein after said collar is fitted to said needle hub via its internal circumferential groove fitting about said flange and a luer end of a medical device mated to said needle hub, said collar is non-removably mated to said needle hub.

20. Needle protection device, comprising:
 a base having a longitudinal axis;
 a housing pivotable relative to said base having two side walls each having an edge for defining a longitudinal slot therebetween;
 locking mechanisms at said base and said housing that coact with each other to retain said housing to said base once said housing is pivoted to a position in alignment with said longitudinal axis; and
 two arms each extending from said base in perpendicular relationship to the edge of a corresponding one of said side walls once said housing is pivoted to said alignment position, said arms preventing said side walls of said housing from being manipulated to sabotage the integrity of said locking means that retains said housing to said base.

21. Device of claim 20, wherein said locking mechanisms comprise one and other locking members at said base and said housing, respectively.

22. Device of claim 20, wherein said arms each extend curvedly from said base to wrap around the edge of its corresponding side wall once said housing is pivoted to said alignment position.

23. Device of claim 20, wherein said base is matingly fitted to a hub having a needle extending therefrom, said device further comprising:
 a latch at said housing for fixedly retaining said needle when said housing is pivoted to the alignment position.

24. Device of claim 20, wherein said collar fits about a flange of a needle hub, said collar having an internal circumferential groove sandwiched by an upper portion and a lower portion, said upper portion being an open ring and said lower portion being a close ring;
 wherein after said collar is fitted to said needle hub via its internal circumferential groove fitting about said flange and a luer end of a medical device mated to said needle hub, said collar is non-removably mated to said needle hub.

25. Needle safety apparatus, comprising:
 a collar having an upper portion and a lower portion separated by an internal circumferential groove, said upper portion being an open ring and said lower portion being a close ring; and
 a housing pivotably connected to said collar at a location away from the opening of said open ring so as to enable said collar to slidably mate to a needle hub via said internal circumferential groove;
 wherein said collar is non-removably fitted to said needle hub once said needle hub is mated with a luer end of a medical device.

26. Needle safety apparatus of claim 25, wherein said housing comprises:
 two side walls for defining a longitudinal slot therebetween, each of said side walls having an edge and a locking portion formed thereat; and
 wherein said collar has extending therefrom two ears each coacting with the locking portion of a corresponding side wall for fixedly retaining said housing to said collar when said housing is pivoted to a position in alignment with a longitudinal axis of said collar.

27. Needle safety apparatus of claim 25, wherein said housing comprises two side walls for defining a longitudinal slot therebetween, each of said side walls having an edge, said apparatus further comprising:
 two arms extending from said collar in opposite directions away from the opening of said upper portion, each of said arms being extended from said collar such that once said housing is pivoted to a position in alignment with a longitudinal axis of said collar, each of said arms would prevent access to a given section of the edge of a corresponding one of said side walls.

28. Needle safety apparatus of claim 25, wherein said collar is matingly fitted to a hub having a needle extending therefrom, said apparatus further comprising:

a latch at said housing for fixedly retaining said needle when said housing is pivoted to said alignment position.

29. Safety device, comprising:

a collar having a longitudinal axis and two ears extending from opposite sides of said collar orthogonal to said longitudinal axis;

a housing having two side walls for defining a longitudinal slot therebetween pivotably connected to said collar, each of said two side walls having a groove or finger that coactingly mates with a corresponding one of said ears when said housing is pivoted to a position in alignment with said longitudinal axis;

two arms each extending from said collar proximately to a corresponding one of said ears to prevent respective sections of edges of said side walls of said housing from being exposed once said housing is pivoted to said alignment position.

30. Safety device of claim 29, wherein said arms each extends curvedly around an edge of its corresponding side wall so as to wrap around the section of the edge of its corresponding side wall once said housing is pivoted to said alignment position.

31. Safety device of claim 29, wherein said collar fits about a flange extending from a needle hub, said collar having an internal circumferential groove sandwiched by an upper portion and a lower portion, said upper portion being an open ring and said lower portion being a close ring;

wherein after said collar is fitted to said needle hub via its internal circumferential groove fitting about said flange and a luer end mated to said needle hub, said collar is non-removably mated to said needle hub.

* * * * *